US00PP12063P2

(12) United States Plant Patent
Roberson

(10) Patent No.: US PP12,063 P2
(45) Date of Patent: Aug. 21, 2001

(54) LANTANA CAMARA PLANT NAMED 'ROBPATHAL'

(76) Inventor: Robert J. Roberson, 31706 E. Pink Hill Rd., Grain Valley, Jackson County, MO (US) 64029

( * ) Notice: Subject to any disclaimer, the term of this patent is extended or adjusted under 35 U.S.C. 154(b) by 0 days.

(21) Appl. No.: 09/350,383

(22) Filed: Jul. 1, 1999

(51) Int. Cl.[7] ..... A01H 5/00
(52) U.S. Cl. ..... Plt./227
(58) Field of Search ..... Plt./227

*Primary Examiner*—Bruce R. Campell
*Assistant Examiner*—June Hwu
(74) *Attorney, Agent, or Firm*—Rothwell, Figg, Ernst & Manbeck

(57) ABSTRACT

This invention relates to a new and distinct *Lantana camara* cultivar which is outstanding because of its: 1) new and unique color transition from gold to orange/pink and finally a lavender/mauve; 2) ease of propagation (approximately 30% quicker than typical *Lantana camara*'s in the market; 3) its rapid growth rate (approximate mature size mound of 42"×42" in one growing season in USDA Zone 5); and, 4) its strong ability to attract butterflies.

2 Drawing Sheets

SUMMARY OF THE INVENTION

This invention relates to a new and distinct *Lantana camara* cultivar which is outstanding because of its 1) new and unique color transition from gold to orange/pink and finally a lavender/mauve; 2) ease of propagation (approximately 30% quicker than typical *Lantana camara*'s in the market; 3) its rapid growth rate (approximate mature size mound of 42"×42" in one growing season in USDA Zone 5); and, 4) its strong ability to attract butterflies. The claimed *Lantana camara* plant was primarily selected for these characteristics. This selection was made from a specially designed Lantana hybridizing program with said hybrid cultivars being planted and grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

Vegetative tip cuttings were taken in January from the original "Mother" plant (produced from seed) and rooted and grown in a greenhouse. These were planted outside as a 2 inch plug size in USDA Zone 5 in the first week of May and grown and observed through September. This outdoor evaluation process was conducted for at least two or more summer growing seasons to observe descriptive characteristics, vigor, cultivar stability, ease of propagation and outdoor or garden performance.

The average wild or naturalized Lantanas, such as varieties found in the southern U.S. and Mexico, set seed at about a rate of one seed per twenty florets. Robpathal sets seed at a rate of about one seed per 1000 florets. This characteristic is desirable for two primary reasons: 1) fewer stray seedlings develop in the landscape, and 2) a lower seed set typically allows for a more continuous bloom display.

Average rooting time for most commercial Lantanas in the market today is about 12 days. Due to the growth vigor of 'Robpathal', the average rooting time is 9 days or about 30% sooner than the average.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America. They are woody ornamentals which are not usually winter hardy North of USDA horticulture Zone 9. The roughish leaves range from yellow-green to green to blue-green and the two basic growth forms are mounding and trailing (weeping). Bloom color usually include yellow, white, cream, pink, or orange.

The cultivar of *Lantana camara* 'Robpathal' may further be described as having a number of distinctive characteristics which are enumerated in the succeeding specific description but broadly stated as comprising; 1) new and unique color transition from gold to orange/pink and finally a lavender/mauve; 2) ease of propagation (approximately 30% quicker than typical *Lantana camara*'s in the market; 3) its rapid growth rate (approximate mature size mound of 42"×42" in one growing season in USDA Zone 5); and, 4) its strong ability to attract butterflies. I have chosen to identify this new cultivar as *Lantana camara* 'Robpathal'. This cultivar is being marketed in the United States under the name of Patriot™ Hallelujah.

BRIEF DESCRIPTION OF THE DRAWING

The accompanying photographs show as nearly true as it is reasonably possible to make the same, in color illustrations of this character, typical leaves and flowers of the new variety. The photographic drawing illustrates the flower form and color and leaf color.

DETAILED DESCRIPTION

Figure 1:
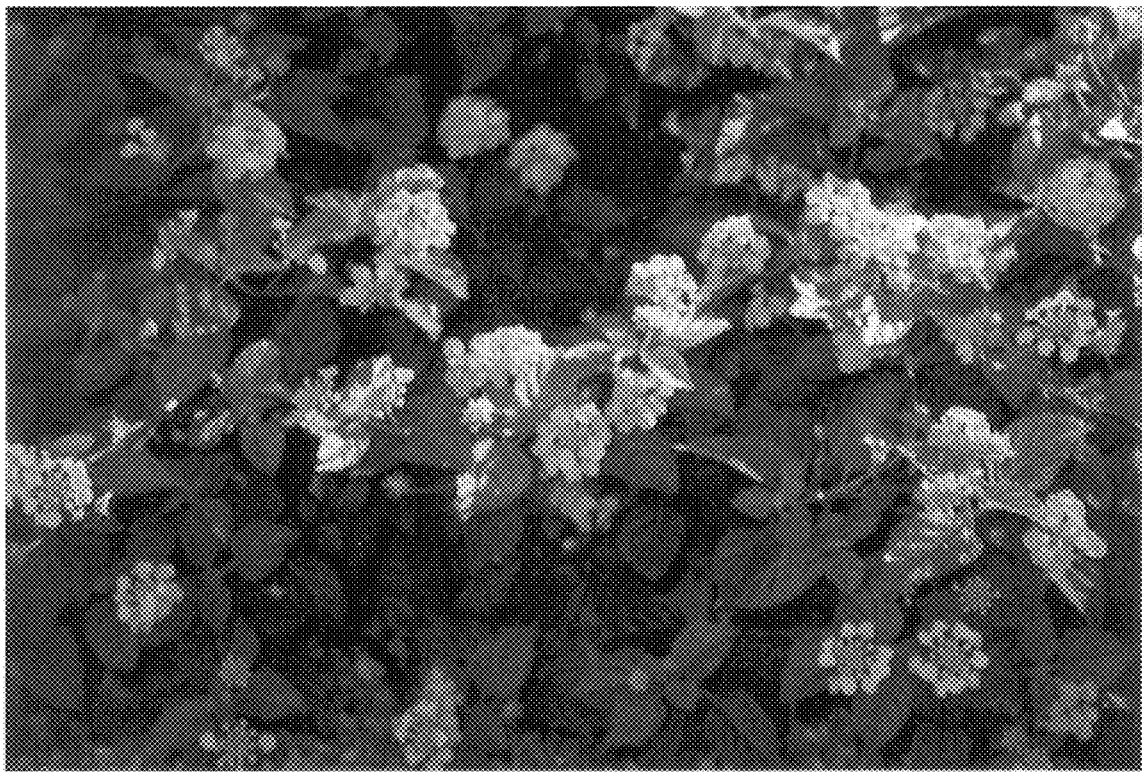
FIG. 1 illustrates the whole plant.
Figure 2:
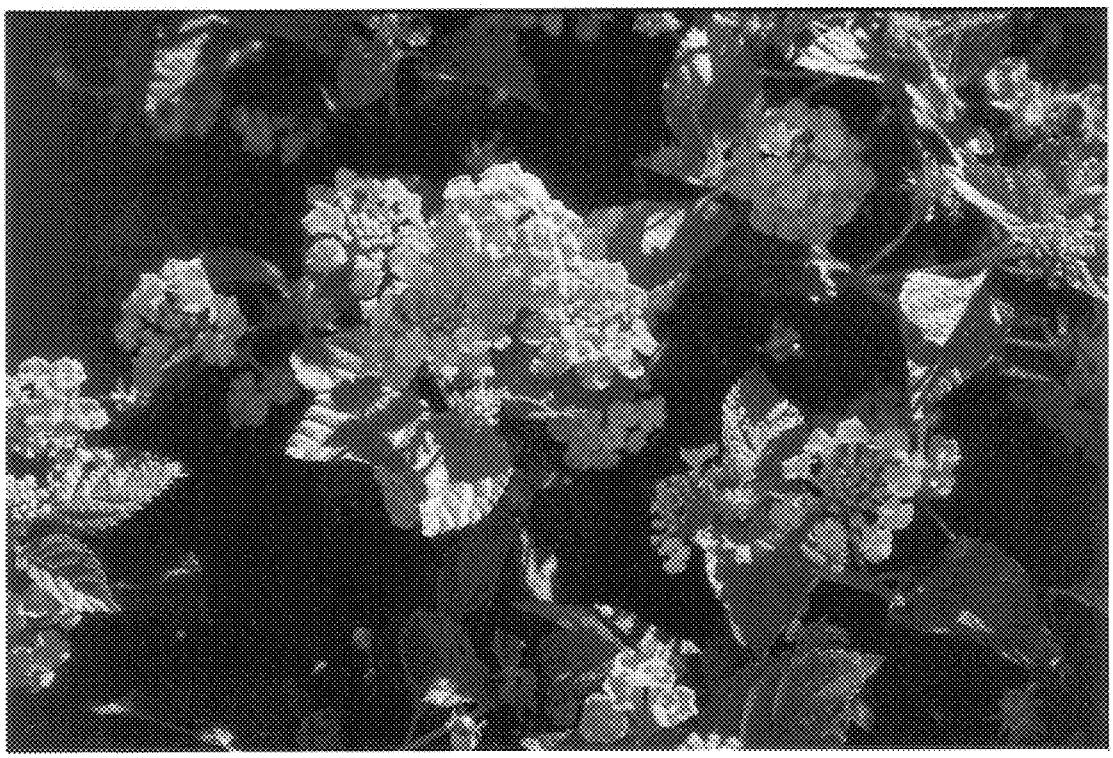
FIG. 2 illustrates the face view of the flower.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature 8 month old plants grown in the vicinity of Grain Valley, Mo.

Parentage:

*Seed parent.*—*Lantana camara* 'Patriot™ Honeylove' (U.S. Plant Pat. No. 10,011) in a semi-controlled open pollination.

*Pollen parent.*—Unknown.

Propagation: Asexual reproduction by tip cuttings started near Grain Valley, Mo.

Plant descriptions:

*Inflorescence and reproductive parts.*—The inflorescence is a flat topped round cluster of 25–30 florets. The individual clusters are determinate and arise from the leaf axils. Each individual floret is slightly un-symmetrical with a bilateral symmetry and is subtended by a single bract. The perianth consist of: the calyx (5 united sepals) and the corolla (5 united petals with narrow tube). The flowers are zygomorphic, hermaphroditic, and have 4 introse stamens which are didynamous. The stamen is approximately 1.2 mm in length. The filament is a glaucous white at the base and transitions to a pale infusion of mauve (PMS #1895) toward the tip. The anther is brown (PMS #4975). The pistil measures approximately 1 mm in length and ⅓ mm diameter on the tip. The base of the pistil is glaucous white and transitions to a pale infusion of mauve (PMS#1895) toward the tip. The ovary is superior, the style is terminal, and the stigma is lobed. The ovary is 2 locular, but is divided into 4 loculi by a false septum in each loculus. The placentation is axile with 2 ovules per carpel. The fruit classification is drupe and potentially contains 2 seeds approximately ⅜" in size with a smooth texture when immature. Mature fruit shrinks to approximately ¼" in size and has a rough texture. When fruit forms, it is green (PMS #363); then matures through a deep purple (PMS #533) to a near black (PMS #532).

Inflorescence dimensions:

*Bloom cluster.*—1.7" in diameter.

*Single floret.*—Range from ⅜"–7/16" in diameter and 9/16" in length.

*Pedicle length.*—1.6".

*Corolla tube.*—0.6" in size; color is cantaloupe (PMS #1555) on the lower portion while the upper portion of the tube transitions with the floret colors.

Inflorescence colors:

*Buds.*—Cantaloupe (PMS #1555); approximately 1/16" when color is first visible to 3/16" just prior to opening.

*First opening.*—Gold (PMS #1225).

*Transitions through.*—Orange/pink (PMS #1565).

*Maturity.*—Lavender/mauve (PMS #1895).

*Transition time.*—4 days (approximately).

*Tube.*—Cantaloupe (PMS #1555) on lower portion with upper portion transitioning with the floret colors.

*Sepal.*—The average sepal size is 3/32" and circular in shape in its distal 50% end, and the proximal end joins together with the other sepal and petals to form the tube which houses the reproductive parts. Color transitions from a canteloupe bud (PMS #1555), to gold (PMS #1225) to a first opening color of orange-pink (PMS #1565) then maturing to a lavender-mauve (PMS #1895).

*Lastingness of the bloom.*—From the opening of the first florets at the periphery of the bloom cluster (inflorescence) to the aborting of the last floret near the center is an average of 6–8 days. This process is shorter with warmer temperatures of about 90–100 degrees Fahrenheit and longer with cooler temperatures of about 65–70 degrees Fahrenheit.

Developmental pattern: First flowers develop in a circular pattern on the periphery of the inflorescence.

Leaves and stems:

*Leaf shape.*—Ovate.

*Leaf margins.*—Serrate.

*Leaf tip and base.*—Acute.

*Leaf veins.*—Pinnate.

*Leaf surface.*—Rough due to bristly hairs.

*Leaf arrangement.*—Opposite.

*Leaf color.*—Immature leaf top surface is PMS #364 with lower surface of PMS #363; mature leaf top surface is PMS #371 with a lower surface of PMS #370.

*Leaf size.*—Length 2.0". Petiole 0.4". Width 1.2".

*Stem.*—Square in youth becoming round and woody with age; immature stems are PMS #363 and measure approximately 1/16" in diameter; mature stems are PMS #4495 in color and approximately ⅛" in diameter; length of internodes ranges from 15/16"–3" and averages 1.9".

*Pubescence.*—Although the pubescence of the leaves and stem are somewhat obscure, it can be noted by close examination with the naked eye on the stem and underside of the leaf. It is more easily distinguished on the upper surface of the leaf. The tube and top surface of the corolla have slightly detectable pubescence.

Roots: Highly branched and fibrous.

*Time to produce a rooted cutting.*—Approximately 9 days in a greenhouse with summer light and approximately 78 degrees Fahrenheit.

Flowering time: The color display begins blooming at 6–7 weeks after cuttings are made, or 4 weeks after potting, and continue until temperatures drop below 45 degrees Fahrenheit.

Fragrance: The inflorescence has a sweet floral fragrance and the leaves have a minty/citrus blend fragrance.

Pests: No known susceptibility to pests noted to date.

Diseases: No known diseases noted to date.

General observations: *Lantana camara* 'Robpathal', with its 1) new and unique color transition from gold to orange/pink and finally a lavender/mauve; 2) ease of propagation (approximately 30% quicker than typical *Lantana camara*'s in the market; 3) its rapid growth rate (approximate mature size mound of 42"×42" in one growing season in USDA Zone 5); and, 4) its strong ability to attract butterflies.

For the purpose of ornamental horticulture in our present living environments which include smaller yards and patio gardening, *Lantana camara* plant "Robpathal" is ideal due to several characteristics:

A. It is an excellent plant for mass planted ground covers, low borders, hanging baskets or focal display containers. *Lantana camara* 'Robpathal' will produce a continuous display of bright, gold colored florets transitioning to orange/pink and finally to a lavander/mauve. This plant remains in bloom when most other flowering perennials' season has ended.

B. The prolific blooming tendency and dense growth habit of this cultivar, with its medium internode spaces provides the garden or landscape with a "fuller", more dense presentation of both foliage and bloom florets; thus making a more dramatic color statement than the average Lantana.

C. This cultivar's slow tendency to set seed allows more continual blooming, and a maintenance of optimum color beauty. This characteristic of being slow to set seed also provides the garden or landscape with a clean environment free of unwanted seedlings.

D. The ease of propagation of 'Robpathal' makes this Lantana a very commercially viable product to serve the horticulture industry.

COMPARISON TO KNOWN VARIETIES

*Lantana camara* plant 'Robpathal' should be compared with *Lantana camara* 'Robpathon' (U.S. Plant Pat. No. 10,011). While similar, there are numerous differences between the claimed Lantana and 'Robpathon' including the fact that 'Robpathal' is a mounded plant form while 'Robpathon' is a weeping, prostrate form. Additionally, the claimed plant's inflorescence colors transition from gold to orange/pink and finally to a lavender/mauve while 'Robpathon' transitions from yellow to salmon and finally a pink/cantaloupe.

I claim:

1. The new and distinct cultivar of *Lantana camara* plant substantially as illustrated and described.

* * * * *